US00PP19258P3

(12) United States Plant Patent
Meilland

(10) Patent No.: US PP19,258 P3
(45) Date of Patent: Sep. 23, 2008

(54) SHRUB ROSE PLANT NAMED 'MEIBOULKA'

(50) Latin Name: *Rosa hybrida*
Varietal Denomination: cv. Meiboulka

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/699,482

(22) Filed: Jan. 30, 2007

(65) Prior Publication Data

US 2008/0155719 P1 Jun. 26, 2008

(51) Int. Cl.
*A01H 5/00* (2006.01)

(52) U.S. Cl. ..... Plt./102

(58) Field of Classification Search ..... Plt./102
See application file for complete search history.

*Primary Examiner*—Annette H Para
(74) *Attorney, Agent, or Firm*—Buchanan Ingersoll & Rooney PC

(57) ABSTRACT

A new and distinct variety of landscape shrub rose plant is provided which forms attractive single bicolored blossoms. The blossom petals are bright red on the upper surface and light pink and red on the under surface. The plant exhibits a bushy growth habit. The attractive dark green and glossy foliage contrasts nicely with the blossom coloration. The new variety is particularly well suited for growing as ornamentation in the landscape.

1 Drawing Sheet

Figures 2, 3, 4, 5, 6, 7, 8, 9, 10, 11, 12, 13, 14, 15, 16:
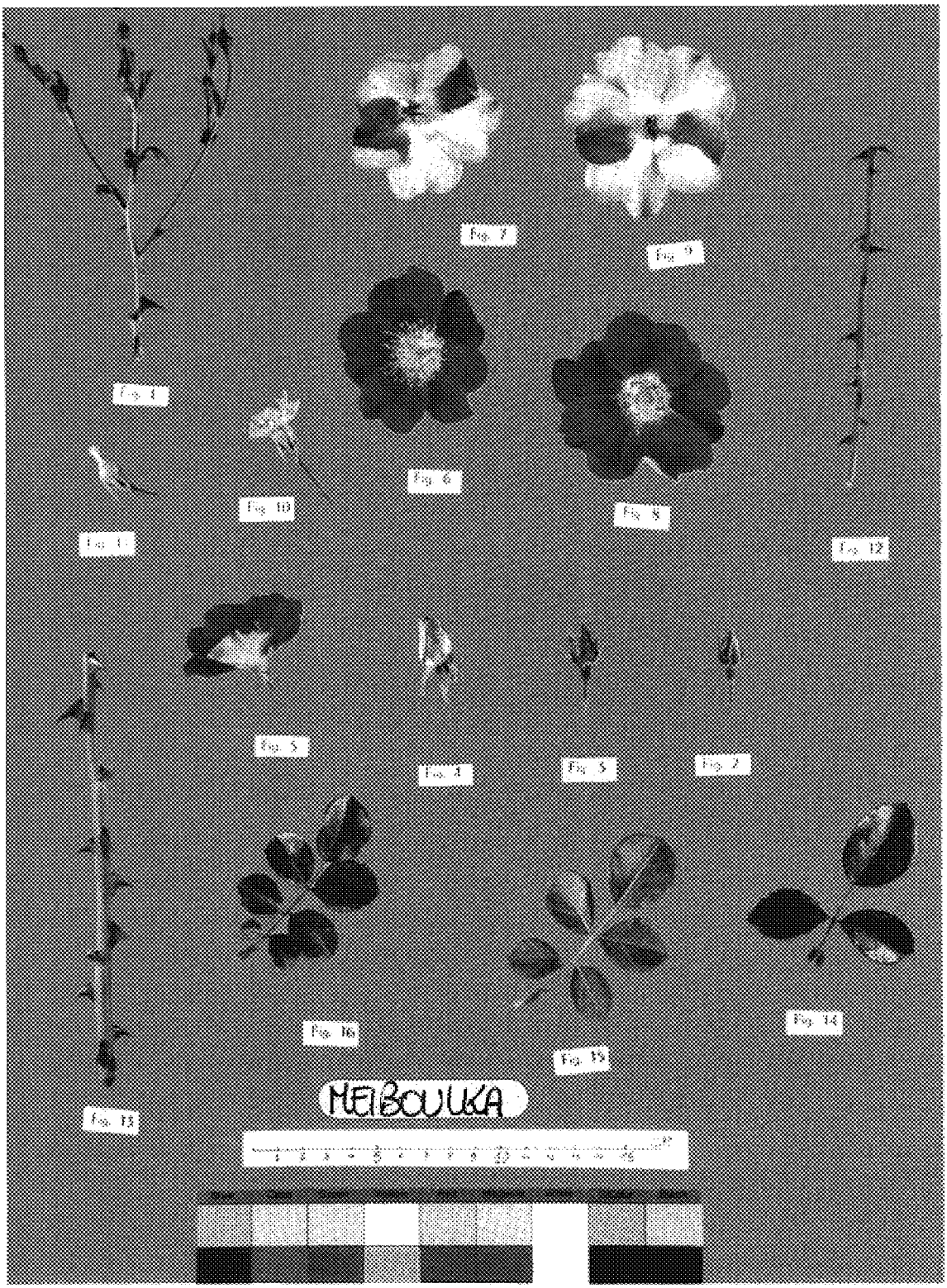

Botanical/commercial classification: *Rose hybrida*/Shrub Rose Plant.
Varietal denomination: cv. Meiboulka.

SUMMARY OF THE INVENTION

The new variety of *Rosa hybrida* shrub rose plant was created by artificial pollination wherein two parents were crossed which previously had been studied in the hope that they would contribute the desired characteristics. The female parent (i.e., the seed parent) was a cross between the 'Kormax' variety (non-patented in the United States) and a non-patented and unnamed seedling. The male parent (i.e., the pollen parent) was the cross between 'Meipoque' variety (U.S. Plant Pat. No. 5,956) and the 'Korimro' variety (non-patented in the United States). The 'Meipoque' variety is being marketed under the PINK MEIDILAND trademark. The parentage of the new variety can be summarized as follows:

('Kormax'×Unnamed Seedling)×('Meipoque'×'Korimro').

The seeds resulting from the above pollination were sown and small plants were obtained which were physically and biologically different from each other. Selective study resulted in the identification of a single plant of the new variety.

It was found that the new shrub rose plant of the present invention (a) exhibits a bushy growth habit, (b) forms attractive single bicolored blossoms wherein the petals are bright red on the upper surface and light pink, and red on the under surface, (c) forms dark green glossy foliage that contrasts well with the blossom coloration, and (d) is particularly well suited for providing attractive ornamentation in the landscape.

The new variety well meets the needs of the horticultural industry. It can be grown to advantage as ornamentation in parks, gardens, public areas, and in residential settings.

The new variety of the present invention can be readily distinguish from its ancestors. For instance, the 'Kormax' variety forms large red blossoms having six petals, the 'Meipoque' variety forms pink blossoms, and the 'Korimro' variety forms white blossoms.

The new variety has been found to undergo asexual propagation in France by a number of routes, including budding, grafting and cuttage. Asexual propagation by the above-techniques in France has shown that the characteristics of the new variety are stable and are strictly transmissible by such asexual propagation from one generation to another.

The new variety has been named 'Meiboulka'.

BRIEF DESCRIPTION OF THE PHOTOGRAPH

The accompanying photograph shows, as nearly true as it is reasonably possible to make the same in a color illustration of this character, typical specimens of the plant parts of the new variety. The rose plants of the new variety were approximately eighteen months of age and were observed during May while budded on *Rosa froebelli* understock and growing outdoors at Le Cannet des Maures, Var, France. Dimensions in centimeters are indicated at the bottom of the photograph.

FIG. 1 - illustrates a specimen of a cluster of floral buds before the opening of the sepals;

FIG. 2 - illustrates a specimen of a floral bud at the opening of the sepals;

FIG. 3 - illustrates a specimen of a floral bud wherein the opening of the sepals of is more advanced;

FIG. 4 - illustrates a specimen of a floral bud at the opening of the petals;

FIG. 5 - illustrates a specimen of a flower in the course of opening;

FIG. 6 - illustrates a specimen of an open flower — plan view — obverse;

FIG. 7 - illustrates a specimen of an open flower — plan view — reverse;

FIG. 8 - illustrates a specimen of a fully open flower — plan view — obverse;

FIG. 9 - illustrates a specimen of a fully open flower — plan view — reverse;

FIG. 10 - illustrates a specimen of a floral receptacle showing the arrangement of the stamens and pistils;

FIG. 11 - illustrates a specimen of a floral receptacle showing the arrangement of the pistils (stamens removed);

FIG. 12 - illustrates a specimen of a flowering stem;

FIG. 13 - illustrates a specimen of a main branch;

FIG. 14 - illustrates a specimen of a leaf with three leaflets — plan view — upper surface;

FIG. 15 - illustrates a specimen of a leaf with five leaflets — plan view — under surface; and FIG. 16 - illustrates a specimen of a leaf with seven leaflets — plan view — upper surface.

DETAILED DESCRIPTION

The chart used in the identification of colors is that of The Royal Horticultural Society (R.H.S. Colour Chart). The description is based on the observation of eighteen month old plants during May while budded on *Rosa froebelli* understock and growing outdoors at Le Cannet des Maures, Var, France.

CLASS: Landscape Shrub.

Plant:

*Habit.*—Bushy.

Branches:

*Young stems.*—Commonly near 0.4 cm in diameter on average.

*Mature stems.*—Commonly near 1.3 cm in diameter on average.

*Thorns.*—Configuration: longish pointed, slightly curved downwards at the tip on the upper surface, and concave on the under surface. Size: long prickles commonly average approximately 1 cm in length, and small prickles commonly average approximately 0.5 cm in length. Frequency: on young stems over a length of 10 cm commonly approximately 9 long prickles and approximately 5 small prickles on average, and on adult stems commonly no prickles are present. Color: long prickles commonly are near Greyed-Orange Group 166B in coloration, and small prickles commonly are near Greyed-Orange Group 164A in coloration.

Leaves:

*Leaflets.*—Number: 3, 5 and 7. Shape: generally elliptic with an obtuse base, and a somewhat cuspidate tip. Serration: single and fine. Texture: firm and consistent. General appearance: dark green and glossy on the upper surface, and lighter green on the under surface.

Inflorescence:

*Peduncle.*—Approximately 3.5 cm in length on average, and approximately 0.2 cm in width on average.

*Sepals.*—Five in number, narrow, longish pointed, approximately 2 cm in length on average, approximately 0.5 cm in width on average at widest point, relatively straight at base, commonly with small extensions having a length of approximately 0.4 cm on average, tomentose on the upper surface, smooth on the under surface, near Yellow-Green Group 145C on the upper surface, and near Yellow Green Group 143A on the under surface.

*Buds.*—Shape: conical. Size: small, approximately 1.6 cm in length on average, and approximately 1 cm in width on average.

*Flower.*—Petalage: single, with rounded tip, weakly reflexed and weakly undulated margin, and approximately 4 cm in length and width. Shape: somewhat flattened when fully open. Color (during course of opening: Upper surface: near Red Group 53A and near Yellow Group 4D at the base. Under surface: near Red-Purple Group 62D, near Yellow Group 11D at the base, and commonly two petals are suffused with Red Group 53A. Color (open flower): Upper surface: near Red-Purple Group 63A suffused with Red Group 53A, and near Yellow Group 4D at the base. Under surface: near Red-Purple Group 62D, near Yellow Group 11D at the base, and commonly two petals are suffused with Red Group 53A. Petal texture: somewhat wavy. Petal arrangement: imbricated. Lastingness: the blossoms commonly last approximately 15 days on average on the plant. Petal drop: good with the petals commonly detaching cleanly before drying. Stamen: approximately 116 in number on average Anthers: regularly arranged around the styles, and near Yellow-Orange Group 15A in coloration. Filaments: near Yellow Group 2D in coloration. Pistils: approximately 28 in number on average. Styles: near Yellow Group 13C in coloration. Stigmas: near Yellow Group 6D in coloration. Hips: commonly approximately 1.5 cm in size and reddish in coloration.

Development:

*Aptitude to bear fruit.*—Present.

What is claimed is:

1. A new and distinct landscape shrub rose plant characterized by the following combination of characteristics:

(a) exhibits a bushy growth habit, (b) forms attractive single bicolored blossoms wherein the petals are bright red on the upper surface and light pink and red on the under surface, (c) forms dark green glossy foliage that contrasts well with the blossoms coloration, and (d) is particularly well suited for providing attractive ornamentation in the landscape;

substantially as herein shown and described.

* * * * *

MEIBOUKA